(12) United States Patent
Rodriguez et al.

(10) Patent No.: US 12,740,779 B2
(45) **Date of Patent: *Sep. 22, 2026**

(54) KNOTLESS ALL SUTURE TISSUE REPAIR

(71) Applicant: ArthroCare Corporation, Austin, TX (US)

(72) Inventors: Christopher Michael Rodriguez, Costa Mesa, CA (US); Tri Nguyen, Garden Grove, CA (US)

(73) Assignee: ArthroCare Corporation, Austin, TX (US)

( * ) Notice: Subject to any disclaimer, the term of this patent is extended or adjusted under 35 U.S.C. 154(b) by 53 days.

This patent is subject to a terminal disclaimer.

(21) Appl. No.: 19/022,087

(22) Filed: Jan. 15, 2025

(65) Prior Publication Data

US 2025/0152162 A1 May 15, 2025

Related U.S. Application Data

(63) Continuation of application No. 18/487,333, filed on Oct. 16, 2023, now Pat. No. 12,256,921, which is a (Continued)

(51) Int. Cl.

*A61B 17/04* (2006.01)
*A61B 17/06* (2006.01)
*A61B 17/00* (2006.01)

(52) U.S. Cl.

CPC .... *A61B 17/0401* (2013.01); *A61B 17/06166* (2013.01); *A61B 2017/00004* (2013.01);

(Continued)

(58) Field of Classification Search

CPC .... A61B 2017/00004; A61B 2017/042; A61B 2017/045; A61B 2017/0459;

(Continued)

(56) References Cited

U.S. PATENT DOCUMENTS 6,585,730 B1 7/2003 Foerster
6,616,684 B1 9/2003 Vidlund et al.

(Continued)

FOREIGN PATENT DOCUMENTS

CN 101073508 A 11/2007
CN 101442944 A 5/2009

(Continued)

OTHER PUBLICATIONS

International Preliminary Report on Patentability (IPRP) PCT/US2012/065103 (WO2013/074691) dated Feb. 5, 2013, 11 pages.

(Continued)

*Primary Examiner* — Phong Son H Dang
(74) *Attorney, Agent, or Firm* — Kate Ryland Tetzlaff

(57) ABSTRACT

A knotless tissue repair assembly for attachment of tissue to bone includes an anchoring implant with a length of suture threaded therethrough. The implant is preferably a soft flexible three-dimensional structure. The implant may be actuated from a first elongate low profile shape into a second short radially expanded shape having a larger diameter than the hole through which it was placed. The suture extends through the anchor, through a tissue to be secured, and back through a designated suture-binding region or passageway within the anchor enabling the suture to be secured therein and without the need for a physician to tie a knot. Further tension applied to a suture leg approximates the tissue to the anchor until a desired tension or distance between the tissue and anchor is achieved.

17 Claims, 9 Drawing Sheets

Related U.S. Application Data continuation of application No. 17/196,535, filed on Mar. 9, 2021, now Pat. No. 11,812,941, which is a continuation of application No. 15/950,387, filed on Apr. 11, 2018, now Pat. No. 10,966,705, which is a continuation of application No. 14/575,120, filed on Dec. 18, 2014, now Pat. No. 9,962,150.

(60) Provisional application No. 61/918,796, filed on Dec. 20, 2013.

(52) U.S. Cl.
CPC ... *A61B 2017/042* (2013.01); *A61B 2017/045* (2013.01); *A61B 2017/0459* (2013.01); *A61B 2017/0462* (2013.01); *A61B 2017/0464* (2013.01); *A61B 17/0485* (2013.01); *A61B 2017/0618* (2013.01); *A61B 2017/06185* (2013.01)

(58) Field of Classification Search
CPC .... A61B 2017/0462; A61B 2017/0464; A61B 2017/0618; A61B 2017/06185; A61B 2017/0414; A61B 2017/0445; A61B 17/0401; A61B 17/06166; A61B 17/0485
See application file for complete search history.

(56) References Cited

U.S. PATENT DOCUMENTS

| | | | | |
|---|---|---|---|---|
| 7,390,332 | B2 | 6/2008 | Selvitelli et al. | |
| 7,905,904 | B2 | 3/2011 | Stone et al. | |
| 7,995,904 | B2 | 8/2011 | Mirsky et al. | |
| 8,506,597 | B2 | 8/2013 | Kaiser et al. | |
| 8,562,847 | B2 | 10/2013 | Yagi et al. | |
| 8,608,777 | B2 | 12/2013 | Kaiser et al. | |
| 9,173,645 | B2 * | 11/2015 | Overes | A61B 17/842 |
| 9,492,158 | B2 * | 11/2016 | Stone | A61F 2/0811 |
| 9,962,150 | B2 * | 5/2018 | Rodriguez | A61B 17/0401 |
| 10,575,842 | B2 * | 3/2020 | Lund | A61L 31/048 |
| 11,426,157 | B2 * | 8/2022 | Song | A61B 17/0401 |
| 12,232,722 | B2 * | 2/2025 | Summitt | A61B 17/0401 |
| 2002/0120270 | A1 | 8/2002 | Trieu et al. | |
| 2004/0012245 | A1 | 1/2004 | Ptasinski | |
| 2004/0122456 | A1 | 6/2004 | Saadat et al. | |
| 2004/0267362 | A1 | 12/2004 | Hwang et al. | |
| 2005/0137624 | A1 | 6/2005 | Fallman | |
| 2005/0192581 | A1 | 9/2005 | Molz et al. | |
| 2006/0178683 | A1 | 8/2006 | Shimoji et al. | |
| 2006/0271073 | A1 | 11/2006 | Lam et al. | |
| 2007/0010857 | A1 | 1/2007 | Sugimoto et al. | |
| 2007/0083236 | A1 | 4/2007 | Sikora et al. | |
| 2007/0219557 | A1 | 9/2007 | Bourque et al. | |
| 2008/0051836 | A1 | 2/2008 | Foerster et al. | |
| 2008/0300683 | A1 | 12/2008 | Altman et al. | |
| 2008/0312689 | A1 | 12/2008 | Denham et al. | |
| 2009/0062847 | A1 | 3/2009 | Ken | |
| 2009/0312776 | A1 | 12/2009 | Kaiser et al. | |
| 2009/0318961 | A1 | 12/2009 | Stone et al. | |
| 2010/0087857 | A1 | 4/2010 | Stone et al. | |
| 2010/0094314 | A1 | 4/2010 | Hernlund et al. | |
| 2010/0203155 | A1 | 8/2010 | Wei et al. | |
| 2011/0022083 | A1 * | 1/2011 | DiMatteo | A61B 17/0469 606/228 |
| 2011/0022084 | A1 * | 1/2011 | Sengun | A61B 17/0401 606/228 |
| 2011/0098727 | A1 * | 4/2011 | Kaiser | A61B 17/0401 606/228 |
| 2011/0118760 | A1 | 5/2011 | Gregoire et al. | |
| 2011/0160767 | A1 | 6/2011 | Stone et al. | |
| 2011/0160768 | A1 | 6/2011 | Stone et al. | |
| 2011/0208239 | A1 * | 8/2011 | Stone | A61B 17/06004 606/228 |
| 2011/0270278 | A1 | 11/2011 | Overes et al. | |
| 2012/0004669 | A1 | 1/2012 | Overes et al. | |
| 2012/0150223 | A1 | 6/2012 | Manos et al. | |
| 2012/0197271 | A1 * | 8/2012 | Astorino | A61B 17/06166 606/232 |
| 2012/0239085 | A1 * | 9/2012 | Schlotterback | A61B 17/0401 606/228 |
| 2012/0245585 | A1 | 9/2012 | Kaiser et al. | |
| 2012/0290002 | A1 | 11/2012 | Astorino | |
| 2012/0290004 | A1 * | 11/2012 | Lombardo | A61B 17/0401 606/232 |
| 2013/0029693 | A1 | 1/2013 | Bradley, Jr. | |
| 2013/0096612 | A1 | 4/2013 | Zajac | |
| 2013/0103082 | A1 | 4/2013 | Kaiser et al. | |
| 2013/0110165 | A1 * | 5/2013 | Burkhart | A61B 17/0401 606/232 |
| 2013/0123810 | A1 * | 5/2013 | Brown | A61B 17/0401 606/144 |
| 2013/0153810 | A1 | 6/2013 | Sealey et al. | |
| 2013/0163810 | A1 | 6/2013 | Wang | |
| 2013/0296895 | A1 | 11/2013 | Sengun | |
| 2013/0296896 | A1 | 11/2013 | Sengun | |
| 2013/0296934 | A1 | 11/2013 | Sengun | |
| 2014/0052178 | A1 * | 2/2014 | Dooney, Jr. | A61B 17/0401 606/232 |
| 2014/0277133 | A1 * | 9/2014 | Foerster | A61B 17/0401 606/232 |

FOREIGN PATENT DOCUMENTS

| | | | |
|---|---|---|---|
| CN | 101961264 | A | 2/2011 |
| CN | 103327910 | A | 9/2013 |
| EP | 2430984 | A1 | 3/2012 |
| EP | 2662031 | A1 | 11/2013 |
| JP | 2012520141 | A | 9/2012 |
| WO | 2012151592 | A2 | 11/2012 |
| WO | 2012151692 | A1 | 11/2012 |
| WO | 2013074691 | A1 | 5/2013 |

OTHER PUBLICATIONS

Search Report and Written Opinion PCT/US2012/065103 (WO2013/074691) dated Feb. 5, 2013, 16 pages.

* cited by examiner

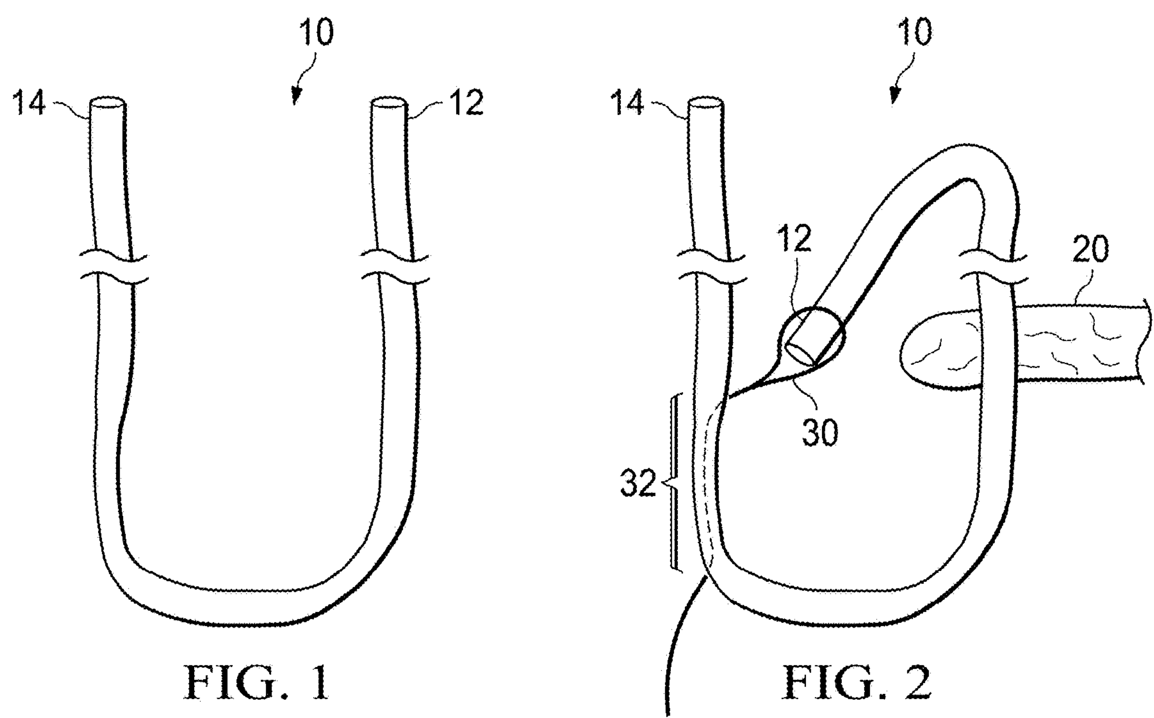
10
14
12
FIG. 1
10
14
12
20
30
32
FIG. 2
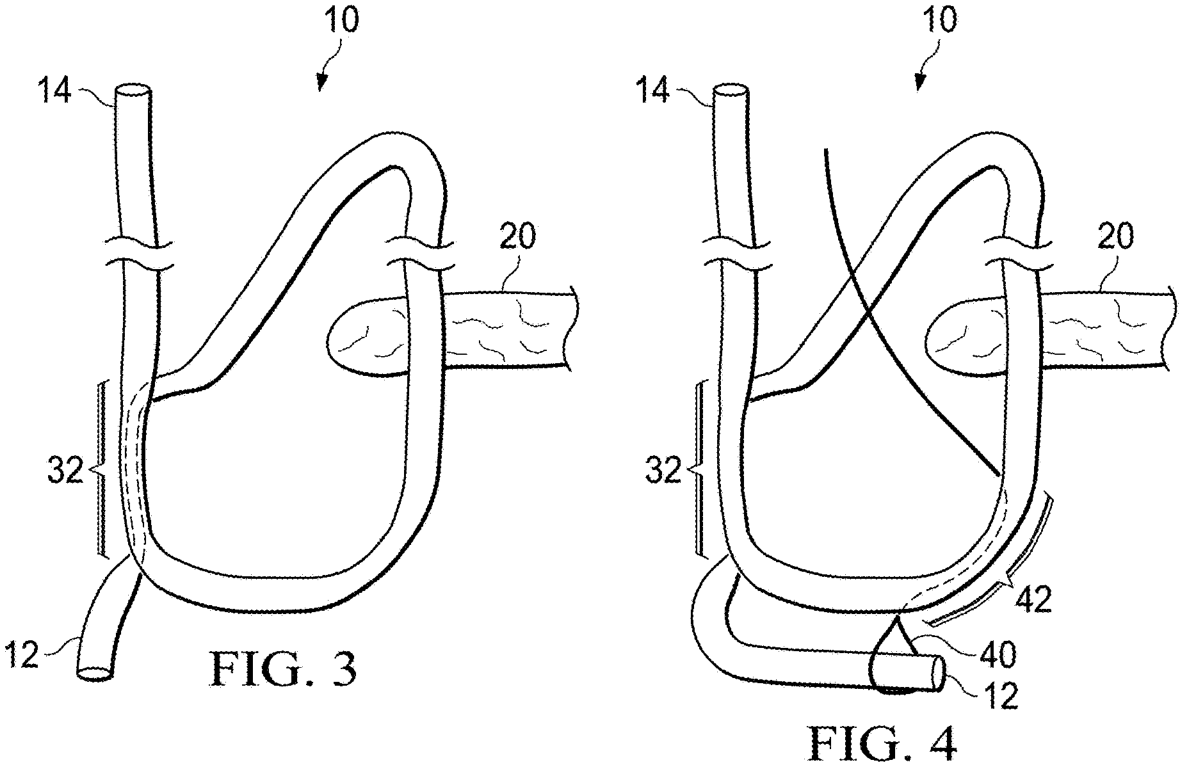
10
14
20
32
12
FIG. 3
10
14
20
32
42
40
12
FIG. 4

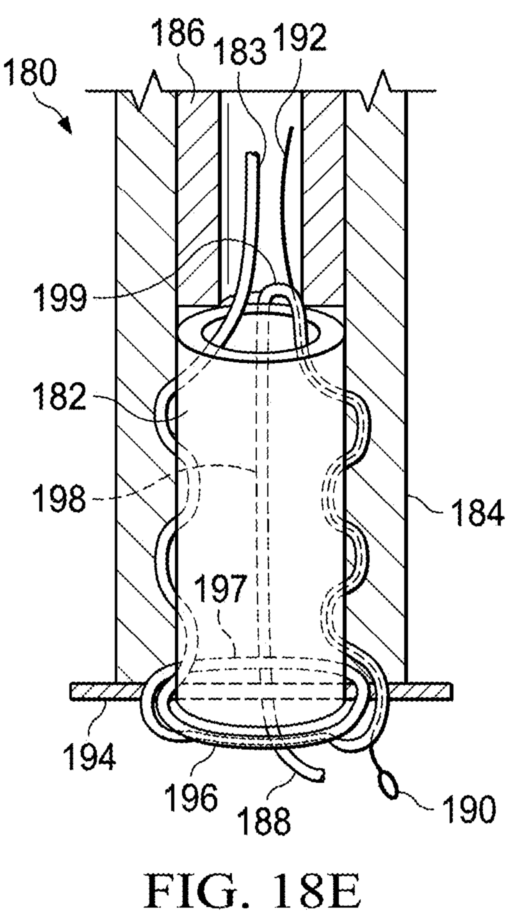
FIG. 18E
204
202
206
200
FIG. 19
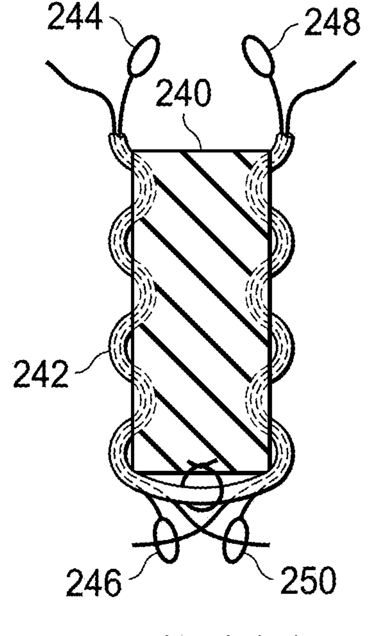
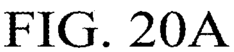
FIG. 20A
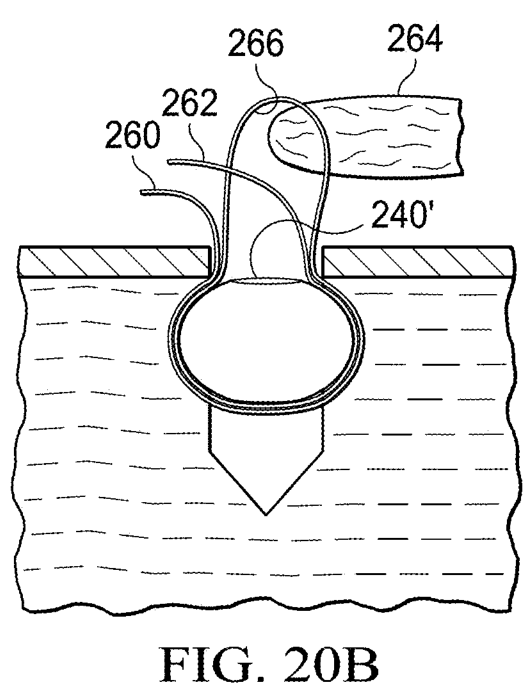
FIG. 20B

KNOTLESS ALL SUTURE TISSUE REPAIR

CROSS-REFERENCE TO RELATED APPLICATIONS

The present application is continuation of U.S. patent application Ser. No. 18/487,333 filed Oct. 16, 2023, entitled "Knotless All Suture Tissue Repair" now U.S. Pat. No. 12,256,921 which is a continuation of Ser. No. 17/196,535 filed Mar. 9, 2021 entitled "Knotless All Suture Tissue Repair, now U.S. Pat. No. 11,812,941 which is a continuation of U.S. patent application Ser. No. 15/950,387 filed Apr. 11, 2018, now U.S. Pat. No. 10,966,705 entitled "Knotless All Suture Tissue Repair," which is a continuation of U.S. patent application Ser. No. 14/575,120 filed Dec. 18, 2014, now U.S. Pat. No. 9,962,150 entitled "Knotless All Suture Tissue Repair," which claims the benefit of provisional patent application No. 61/918,796, filed Dec. 20, 2013, entitled "Knotless All Suture Anchor", all of which are incorporated herein by reference. This application is also related to PCT application number PCT/US2014/071164 filed Dec. 18, 2014.

BACKGROUND OF THE INVENTION

There is an increasing demand for more types of minimally invasive surgical techniques. Because endoscopic and arthroscopic surgery tends to result in lower morbidity than open surgery, the minimally invasive surgical techniques are very appealing to both patients and physicians. These technologically-advanced procedures include many forms of soft tissue to soft tissue repairs and soft tissue to bone repair. Examples of these (procedures in orthopedic surgery include rotator cuff repair, labral repair, biceps tenodesis, and anterior cruciate ligament reconstruction. Other examples in other surgical subspecialties include, but are not limited to, hernia repair, hysterectomies, and laparoscopic gastric bypass.

Many orthopedic surgery procedures involve the use of anchoring devices that attach soft tissue to bone. Most of these procedures and techniques rely on the use of polymers, metal, or biodegradable compounds. The use of these materials often requires relatively large holes placed in bone. Conventional (knotted) suture anchors utilize a sliding arthroscopic knot (ex: SMC, Weston, etc) plus the addition of up to 6 alternating half hitches. This knot stack can be up to 10 mm high, and cause irritation in some patients. If these devices ever loosen, one is faced with the issue of having a potentially hard device in a joint, which can place the patient at risk for developing arthritis. Certain polymeric devices, such as those made with polylactic acid (PLA), can weaken bone, predisposing the patient to fracture. Finally, metal devices can cause scatter on MRI, making follow-up MRI's inaccurate.

Additionally, two major challenges facing all surgeons, and endoscopic surgeons in particular, are knot tying and suture management. Use of multiple sutures can lengthen procedure time, producing higher risk to the patient and lower repair predictability. Endoscopic knot tying is also very challenging. For example, arthroscopic soft tissue biceps tenodesis requires multiple passes of suture through the tendon and rotator cuff, followed by retrieval and knot tying which require a great deal of skill.

Solutions have been developed as an alternative to complex suture management, particularly for soft tissue to bone fixation. For example, a knotless anchoring assembly and method that uses only soft, flexible materials in repairs has a number of advantages including: 1) the use of a less-invasive techniques for implantation because the use of a material that is less brittle allows the use of smaller holes in bone; 2) the ease of MRI use in follow-up; 3) no risk of a hard device lodging in a joint or body cavity; 4) potentially better tissue incorporation, 5) stronger bone and lower risk of bone fracture; 6) the elimination of sophisticated knot-tying, and 7) elimination of the high profile knot stack, which may cause irritation.

SUMMARY OF THE INVENTION

The description, objects and advantages of the present invention will become apparent from the detailed description to follow, together with the accompanying drawings.

A knotless anchor for securing a tissue to a bone or tissue to tissue in a human or animal includes an implant for inserting into the bone and a suture for joining the tissue to the implant. The suture is looped through the tissue, and drawn through a soft suture-locking tunnel present within the implant. Applying a first force in the proximal direction to the loop of suture causes the first suture-locking tunnel to radially decrease thereby binding the suture and prohibiting the first loop from expanding. Applying tension to a first and second end of the suture causes the anchoring implant to change from a first elongate, radially narrow, configuration to a second axially shortened, radially extended, configuration. When the anchoring implant is located in the bone hole, the anchoring implant may be expanded to its second configuration, thereby locking it in the bone hole.

In embodiments, the suture is fed back into itself, and the suture-locking tunnel is comprised of an intermediate length or portion of the suture between the suture ends.

In embodiments, the anchor further comprises a second soft elongate suture-locking tunnel, and wherein applying tension to the first loop causes each of the first and second suture-locking tunnels to radially decrease thereby locking the suture and prohibiting the first loop from expanding.

In embodiments, the suture is a braid.

In embodiments, the anchoring implant is a braided structure.

In embodiments, the anchoring implant has a tubular structure when in the first configuration.

In embodiments, the suture is at least partially interwoven along the sidewalls of the anchoring implant.

In embodiments, the anchoring implant and the first suture consist of biodegradable materials.

In embodiments, the anchoring implant is made of a hard material.

In embodiments, an anchor assembly for securing tissue to a bone or tissue to tissue of an animal or human comprises an anchoring implant for inserting into the bone or tissue, a first suture extending through the anchoring implant, a first suture-locking cradle; and a first snare extending through the first suture-locking cradle. The first snare draws a first end of the first suture through the suture-locking cradle to form a first suture loop through the tissue, wherein applying tension to the first suture loop actuates the first suture locking cradle to bind the first suture therein, thereby prohibiting the first suture loop from expanding. Applying tension to a terminal end of the suture when the anchoring implant is located in the bone causes the anchoring implant to change from the first configuration into a second configuration comprising an axially shortened, and radially extended shape so as to lock the anchoring implant in the hole.

In embodiments, the anchor assembly further comprises a second snare extending through a second suture-locking cradle located along the suture, and for drawing the first end of the first suture therethrough.

In embodiments, the anchor assembly is configured such that when the first end of the first suture is drawn through the first suture-locking cradle so as to form the first suture loop through the tissue, the first suture extends from the tissue, along an exterior surface of the sidewalls, and into the anchoring implant at the distal end of the implant.

In embodiments, the anchor assembly further comprises an elongate inserter tube, the anchoring implant being disposed within a distal lumen of the inserter tube.

In embodiments, the anchor assembly further comprises an inner push member located in the inserter tube. The push member comprises a stop surface in opposition to the proximal end of the anchoring implant, and wherein the inserter tube is axially moveable relative to the push member.

In embodiments, the anchor assembly further comprises a pin between the inserter tube and the distal end of the anchoring implant. The pin is adapted to prevent substantial distortion of the anchoring implant when the first end of the first suture is drawn by the first snare.

In embodiments, the anchoring implant comprises a soft braided structure.

In embodiments, the anchor assembly comprises a knot or loop between the anchoring implant and the first suture.

In embodiments, a method of anchoring a tissue to a bone of a human or an animal without tying a knot comprises: creating a hole into the bone; passing a first end of a suture through the tissue; drawing the first end of the suture through a first suture-locking cradle at least partially located in an anchoring implant thereby forming a first loop of suture extending from the proximal end of the anchoring implant, through the tissue, and returning to the anchoring implant, wherein the suture-locking cradle comprises a soft elongate passageway; inserting the anchoring implant into the hole; deploying the soft anchoring implant in the hole; and approximating the tissue to the soft anchoring implant.

In embodiments, the method further comprises actuating the first suture-locking cradle to create a binding interface with the suture disposed therein, prohibiting the first loop from being enlarged.

In embodiments, actuating is performed prior to the step of deploying. In other embodiments, the step of actuating is performed by pulling proximally on at least one of a) the tissue and b) the suture connected to the tissue.

In embodiments, the inserting step comprises inserting an anchoring implant having a soft braided structure into the hole.

In embodiments, the suture is at least partially interwoven along the sidewalls of the anchoring implant.

In embodiments, approximating the tissue is performed by decreasing the size of the first loop.

In embodiments, decreasing the size of the first loop is performed by pulling on the first end of the suture.

In embodiments, pulling on the first end of the suture comprises tensioning the suture to a predetermined force.

In embodiments, deploying is performed by shortening axially and expanding radially the anchoring implant.

In embodiments, the deploying is performed by pulling on at least one of the first suture end and a second suture end extending proximally from the anchoring implant.

In embodiments, the method further comprises drawing a second end of the first suture through a second suture-locking cradle disposed in the anchoring implant, thereby forming a second loop of suture extending from the proximal end of the anchoring implant.

In embodiments, the drawing is performed by capturing the first end of the suture in a wire loop of an elongate snare.

In embodiments, the deploying step comprises pulling the soft anchoring implant against a die to expand a cross section of the soft anchoring implant.

BRIEF DESCRIPTION OF THE DRAWINGS

FIGS. 1-6 are side views of a single suture, and illustrate the formation of a plurality of suture locking regions along the suture path;

FIG. 18E is a cross sectional view of an anchor assembly including tools for snaring the suture tail, advancing the implant into a bone tunnel, deploying the implant in the bone tunnel, and approximating the tissue to the bone;

FIG. 19 is a side view of a soft anchoring implant in a bone tunnel comprising a plurality of sutures and a suture locking cradle exterior to the anchor body;

FIG. 20A is a side view of a soft anchoring implant comprising a first suture for creating two distinct suture binding regions;

FIG. 20B is a side view of the soft anchoring implant shown in FIG. 20A, shown loaded with a second suture and deployed in a bone tunnel;

DETAILED DESCRIPTION OF THE INVENTION

Figure 5:
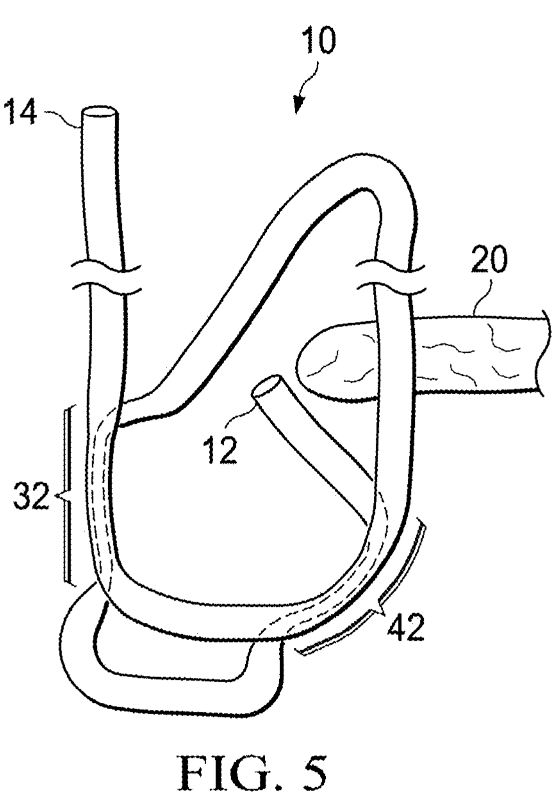

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

A suture anchoring implant for securing soft tissue to bone, or tissue to tissue is described herein. In embodiments, the anchor is a soft all suture implant. A suture extends through the anchor, through a tissue to be secured, and back through a designated suture locking region or passageway within the anchor enabling the tissue to be secured and without the need for a physician to tie a knot.

FIGS. 1-6 illustrate the formation of a plurality of suture locking regions along a length of suture in accordance with one embodiment of the invention. The anchoring implant is not shown in FIGS. 1-6 to facilitate understanding of the suture path and locking mechanics.

With reference first to FIG. 1, a length of hollow braided suture 10 commences at a first suture end 12 and terminates at a second suture end 14. The ends define a suture length therebetween.

In a procedure, a surgeon passes the first suture end 12 through the tissue to be reattached. To pass the suture through the tissue, a wide variety of techniques may be employed including, without limitation, use of the suture passer described in U.S. Publication No. 2011/0118760 to Gregoire et al.

With reference to FIG. 2, a first snare 30 is shown routed through a portion 32 of the length of suture. The snare 30 may be a wire member comprising a loop. An example of a snare and hollow braided suture is shown in U.S. Pat. No. 6,296,659 to Foerster.

The first suture end 12, which has been passed or looped around the tissue, is placed within snare 30, so that the snare may draw the first suture end between the suture braids and into the lumen of the length of suture. The first suture end 12 may be drawn along the suture lumen in a direction away from the second suture end 14 before exiting the suture lumen a short distance later. As will be described further herein, the region 32 along the suture length creates a binding interface, suture cradle, or first friction lock region when actuated.

With reference to FIGS. 3-4, the first suture end 12 is snared again in a similar manner to that described in FIG. 2 using a second snare 40. The second snare is prepared or pre-routed so as to draw the first suture end 12 back through the braids and inside the lumen of the suture. More specifically, the first suture end 12 may be drawn into the lumen of the suture at a location between the first friction lock area 32 and the tissue and weave in a direction again towards the tissue, before exiting the lumen of the suture to create a second friction lock zone 42. As will be described further herein, the region 42 along the suture length may create a second binding interface, suture cradle, or friction lock region when actuated.

Figure 6:
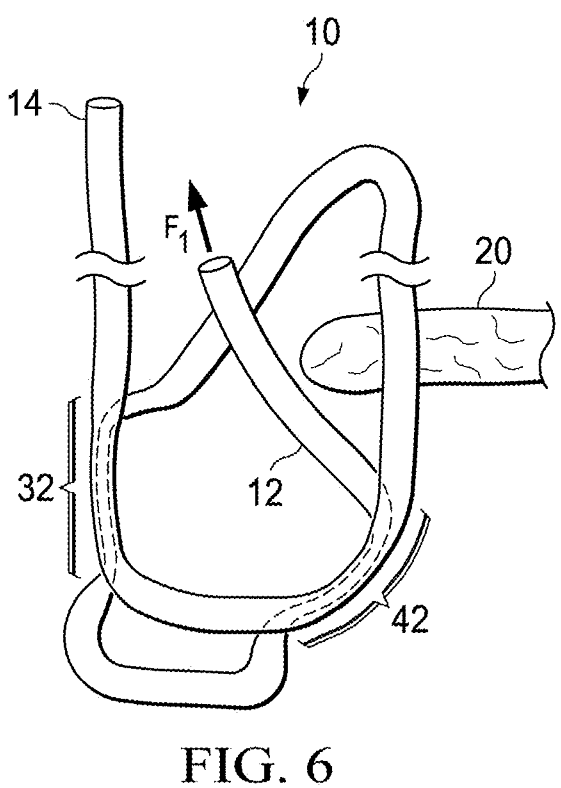

With reference FIGS. 5-6, two distinct friction lock areas 32 and 42 have been prepared. The suture 10 now has two suture ends 12, 14 defining a length of suture in a looped configuration with the tissue 20 and two friction locks areas 32, 42. When a load is applied to either the first suture end 12 or second suture end 14, or the tissue 20, the suture along the first and second friction lock areas 32, 42 will constrict, bind to itself, and thereby prohibit the loop from expanding. Additionally, the first suture end 12 may be pulled by the user with a Force ($F_1$) to reduce the length or size of the loop until the tissue is approximated as desired.

Soft Anchor with Plurality of Suture Locking Regions

FIGS. 7-14 illustrate a soft anchoring implant, and formation of a plurality of suture locking regions along a length of suture for knotless reattachment of tissue to bone.

Figure 7:
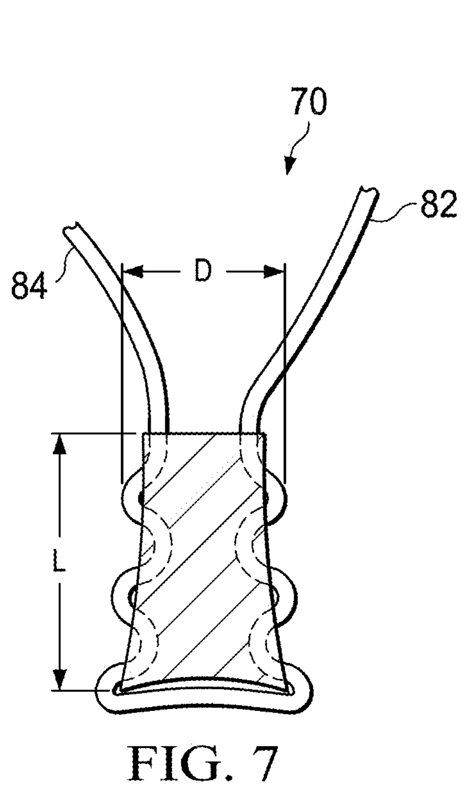
FIGS. 7-12 are side views of a soft anchoring implant, and illustrate the formation of a plurality of suture locking regions along the suture path.

With reference first to FIG. 7, a soft anchoring implant 70 in accordance with one embodiment of the invention is shown. The soft anchoring implant 70 may be a three-dimensional tubular shape. The anchor may have one open proximal end and one closed distal end. Exemplary non-limiting dimensions for the implant are in the range of 10 mm-30 mm in length and 2 mm-6 mm in width or diameter.

Preferably, an anchoring implant has a first pre-deployed state in which fibers are relaxed in an elongated state. The fibers of the implant are more aligned in an orientation parallel to a longitudinal axis and are generally more concentrated. In this orientation, the soft anchoring implant is generally in an elongated state and of a generally small diameter with an exemplary width or diameter "D" of 0.06" to 0.150" and length "L" of 0.5" to 1.0". The implant may be pulled and manually manipulated to achieve this configuration or the use of specialized manufacturing fixtures may be employed, such as a funnel, tube and/or pin, which may compel the implant to achieve this first configuration to better fit within an inserter tube.

In embodiments, the anchor implant is formed from a coarse braided material. The structure utilized may be a cylindrical, helically wound braid, such as the common biaxial braid. Pulling the entire braid along its length (i.e., putting the braid in tension) lengthens and narrows it. The length (L) is gained by reducing the angle between the braided threads of the wound braid at the crossing points of the threads so that the braided threads align mostly parallel, which also reduces the radial distance between opposing sides and hence the overall circumference. When counter traction occurs, the opposite action occurs, and the braid longitudinally contracts axially and expands radially, in this case by increasing the angle between the braided threads. This helically wound braid provides an advantage in that the structure can collapse and elongate naturally due to the alignment of the braids. Non-limiting examples of a soft anchoring implant include the Q-Fix™ all suture implant manufactured by ArthroCare Corporation, Texas, USA, and is generally described in U.S. Publication No. 2013/0123810.

With reference again to FIG. 7, and prior to inserting the anchoring implant 70 into the bone tunnel, a length of suture is threaded through the anchoring implant, using a snare as mentioned herein. A suture end may be passed in a generally distal direction so as to be interwoven in and out of the anchor implant wall, between the material threads in the implant wall but not necessarily into the threads. The suture ends 82, 84 extend or snake through a portion of the anchor implant wall all the way to the implant distal end and then return using a similar weaving pattern through the wall on the opposing side of the anchor so as to exit the anchor implant at the proximal end. This results in a first suture end 82 and a second suture end 84, with the length of suture therebetween interwoven within the anchor implant 70. If suture ends 82, 84 were to be pulled at his point, the soft anchor implant 70 would shorten in length and expand radially.

However, prior to deploying the soft anchor, the plurality of suture locking zones or cradles are formed. As described further herein, the suture is fed or drawn into itself in order to form the plurality of knotless suture locking regions.

FIGS. 8-12 illustrate formation of the knotless first and second suture locking regions 86, 96 through the soft anchoring implant 70.

Figure 8:
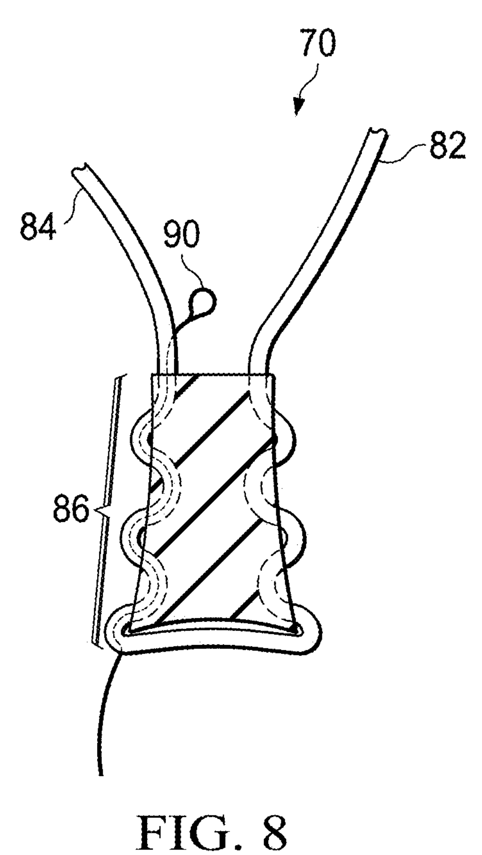
Figure 9:
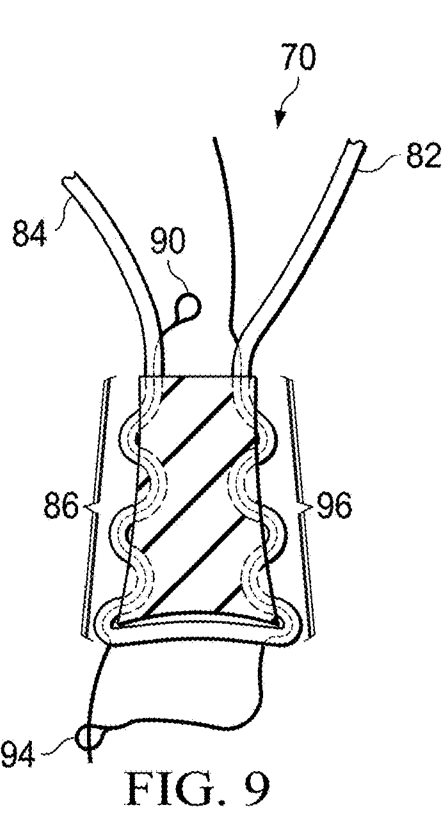

FIG. 8 shows a first snare 90 extending (or drawn) through the lumen of the suture locking region 86 of suture that is interwoven within the implant wall. FIG. 9 shows a second snare 94 extending through the lumen of the suture locking region 96 that is disposed on the opposing side to suture locking region 86.

Figure 10:
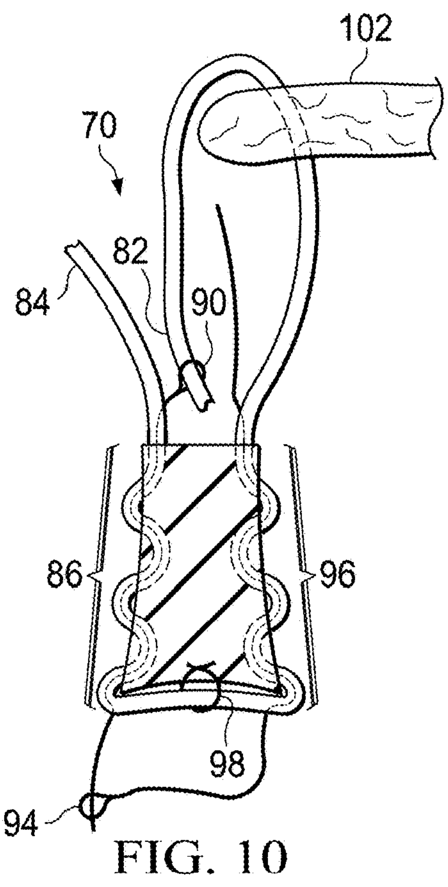

FIG. 10 shows a suture strand end 82 passed through the tissue 102 and in the first snare 90. The snare 90 may now be pulled distally, drawing the suture end 82 through the first half of the anchor, creating the suture friction lock 86.

Figure 11:
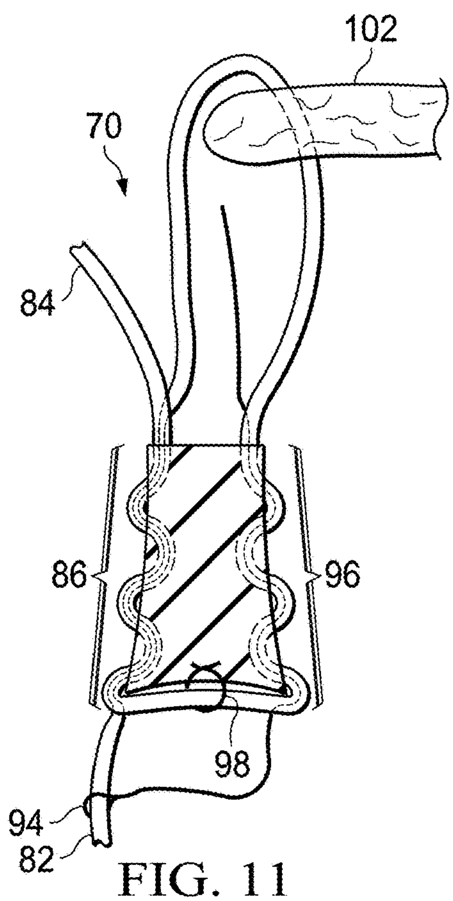

FIG. 11 shows the first suture end 82 positioned in second snare 94. The snare 94 may now be pulled proximally, drawing the tail of strand 82 through the friction lock 96.

Figure 12:
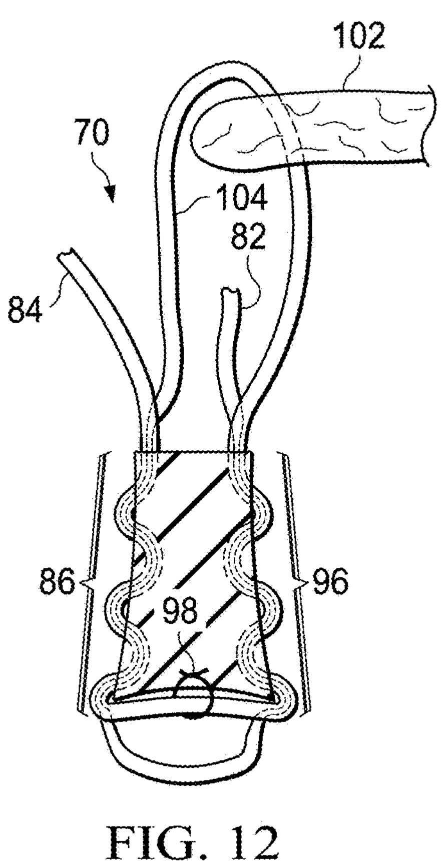

FIG. 12 shows the tissue 102 inside the loop created by the length of suture extending from the anchor implant 70. Two distinct friction locking zones or mechanisms 86, 96 have been created. As described herein, the plurality of suture locking zones may be actuated by, for example, pulling on the tissue loop 104, or the tissue 102 itself. When the loop is pulled, the first and second suture locking cradles 86, 96 narrow, thereby binding the loop in place and without tying a knot. The suture loop is prohibited from expanding when the tissue is pulled.

Also shown in FIG. 12 is a distal tie, loop or knot 98. Knot 98 may be placed between the suture strand and the soft anchor body. Knot 98 is preferably placed towards the center of the length of suture and the anchor body. Knot 98 serves to maintain the suture locking mechanisms inside the anchor implant and bone tunnel.

Figure 13:
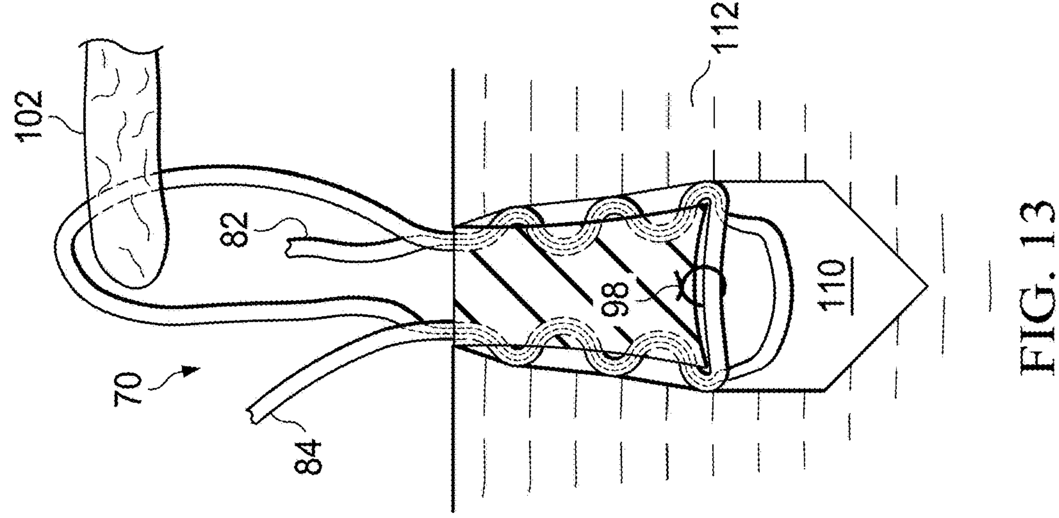
FIG. 13 is a side view of the soft anchoring implant shown in FIG. 12 inserted in a bone tunnel.

FIG. 13 shows inserting the loaded implant 70 into a hole 110 within a bone 112. This step may be done manually using instruments including hand held inserter tubes, guides, and advancers or dies (not shown in these figures for facilitating illustration of the internal suture locking mechanisms).

Figure 14:
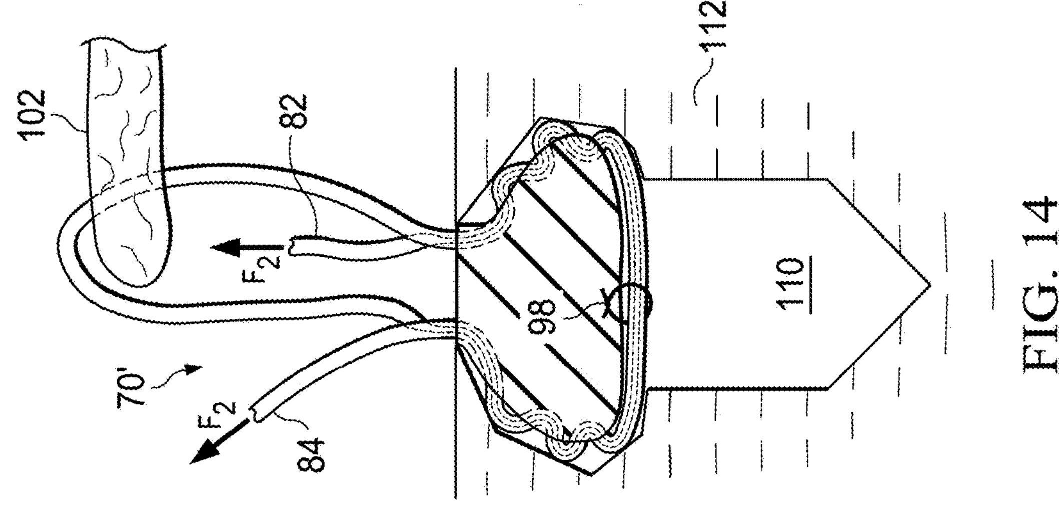
FIG. 14 is a side view of the soft anchoring implant shown in FIG. 13 in a radially expanded bone-lock configuration.

FIG. 14 shows deploying the anchor by pulling first and second suture ends 82, 84 with force ($F_2$). A die instrument (not shown) may be positioned against the proximal end of the anchor 70' to constrain the anchor in the tunnel and prohibit its upward movement. As shown, the anchor implant expands to a second deployed configuration 70' underneath the cortical layer of the bone, creating a bone lock.

Figure 15:
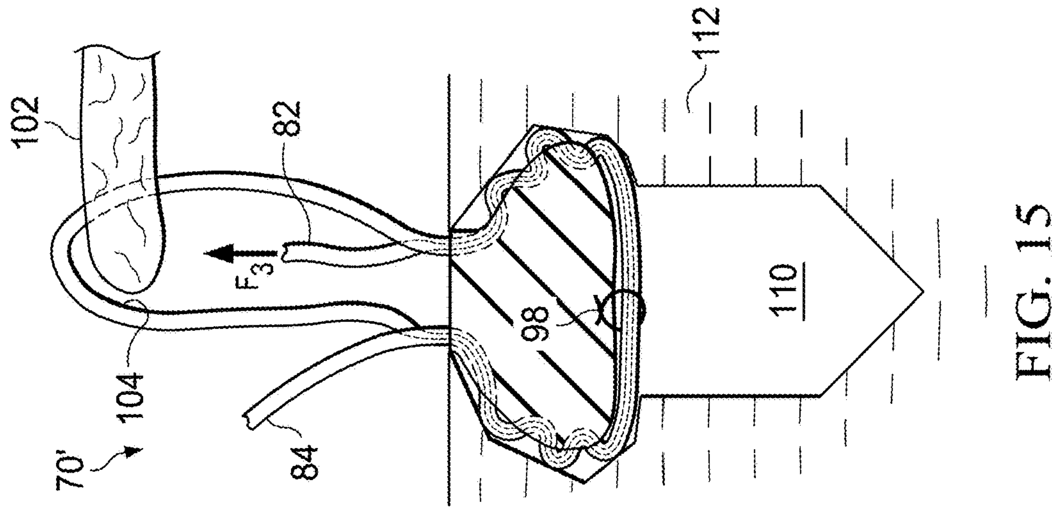
FIGS. 15-17 are side views, illustrating approximating a tissue to the soft anchoring implant shown in FIG. 14.
Figure 17:
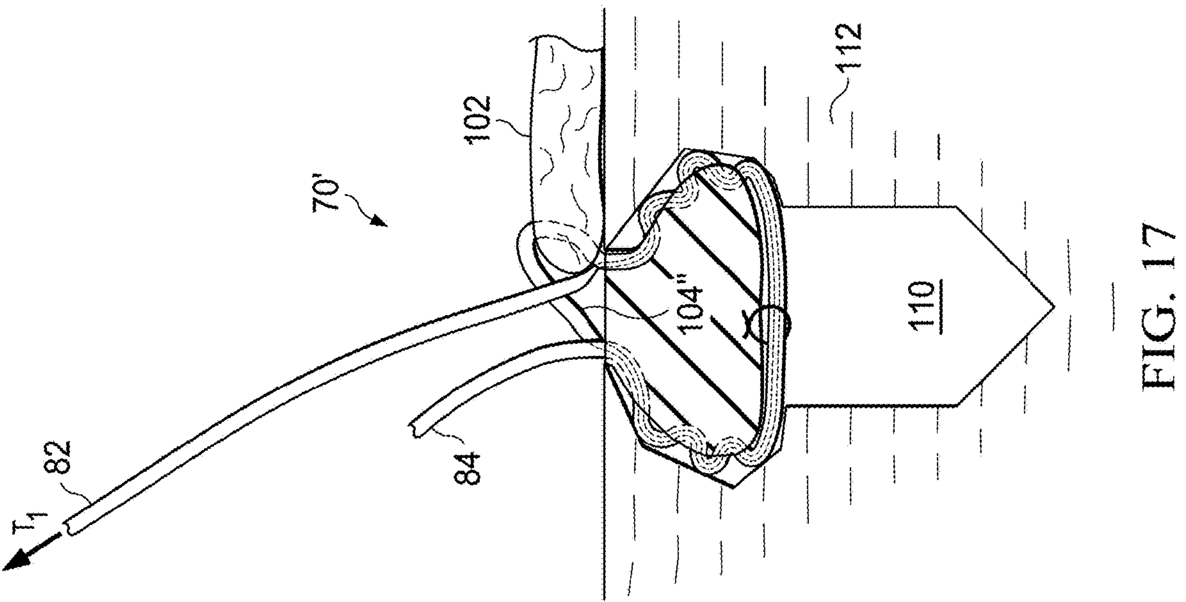
Figure 16:
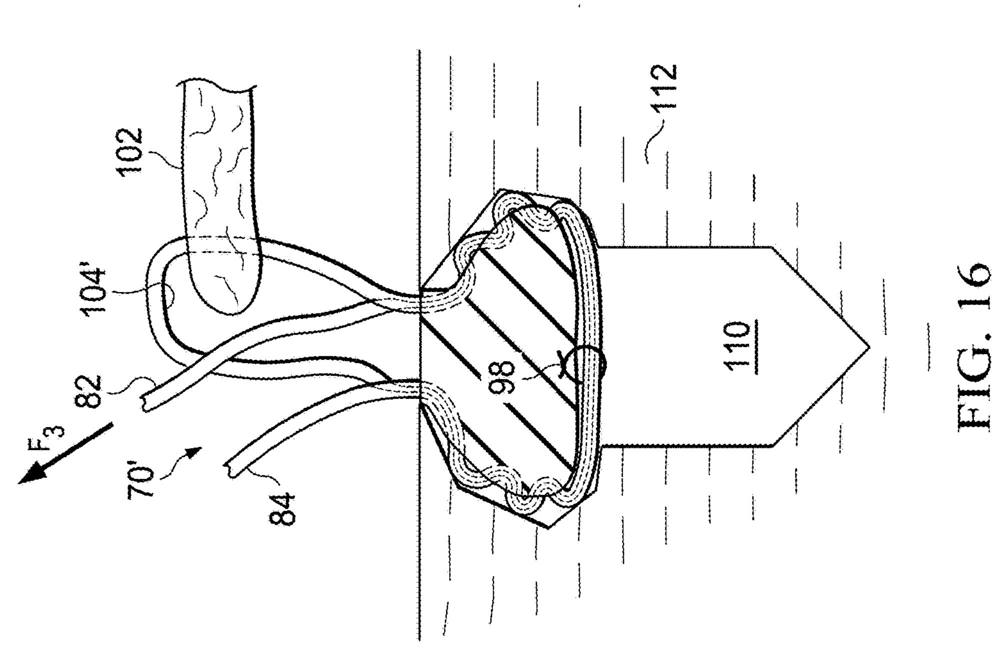

FIGS. 15-17 show approximation of the tissue 102 to the bone 112. The surgeon may pull on the first suture end 82 to further reduce the loop 104 to a smaller loop 104', and yet smaller loop 104" corresponding to FIGS. 16 and 17 respectively. The surgeon may further pull on the first suture end 82 until a desired tension force $T_1$ of the tissue 102 to the anchoring implant and bone is created. First and second suture ends may be trimmed.

Soft Anchor with Single Suture Locking Region

The tissue repair assemblies and implants may have a plurality of suture locking regions as described above, or in embodiments, the implant may have less than a plurality of suture locking regions.

Figure 18A:
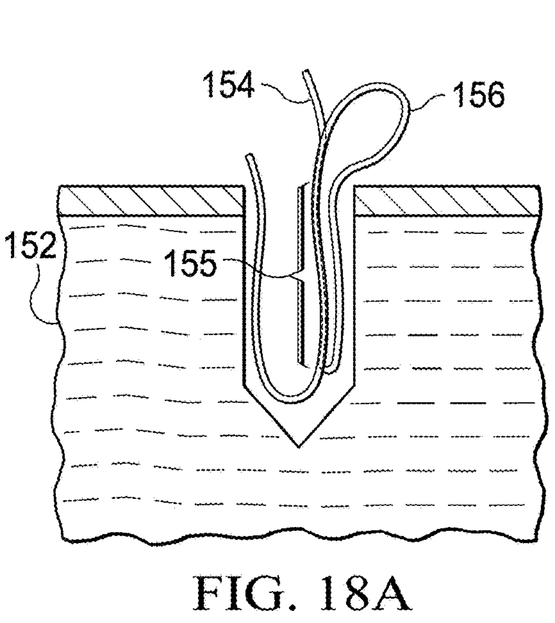
FIG. 18A is a side view of a single suture, and illustrates the formation of a single suture locking region along a suture path.

With reference to FIG. 18A, for example, a suture locking mechanism is shown and described having only one friction lock region. FIG. 18A shows the suture strand in a hole in a bone 152, the anchor implant being removed for facilitating understanding of the suture path. The suture friction lock 155 is shown on the same side as the tissue loop 156. However, in embodiments, the sole friction lock may be disposed opposite the tissue loop, or on another side of the implant. The suture may be threaded as described above, except that only one snare loop and friction lock region are made.

Figure 18B:
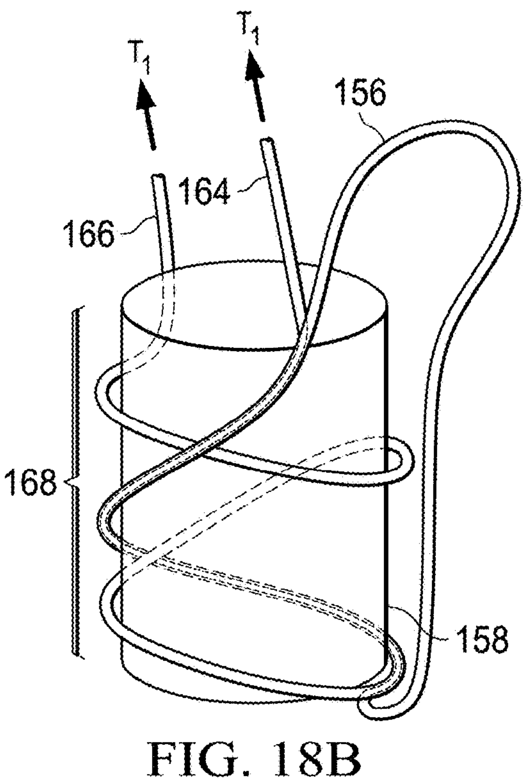
FIG. 18B is a perspective view of a soft anchoring implant comprising a serpentine shaped suture path and associated suture locking region.

FIG. 18B shows another embodiment having a suture interwoven with a soft anchor implant 158. The suture extends across the anchor body in a zig zag or circumferential pattern. The suture is fed back into itself at the distal end of the anchor, and out the proximal end of the anchor. Tension on the suture loop 156 narrows the suture, creating a suture lock along region 168. Applying tension $T_1$ to first end and second end 164, 166 serves to lock the suture.

Figure 18C:
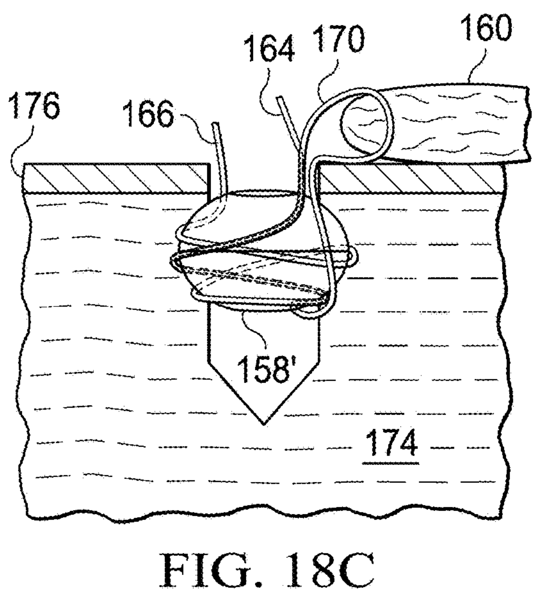
FIG. 18C is a side view of the soft anchoring implant shown in FIG. 18B, deployed in a bone tunnel.

FIG. 18C shows the anchoring implant of FIG. 18B deployed in a tunnel in bone 174. Tension is applied as described above to expand the profile of the implant from an elongate linear shape 158, to a 3-dimensional spherical shape 158'. Desirably, the implant is enlarged in the soft cancellous bone tissue 174, below the relatively hard cortical bone layer 176. Pulling further on the first suture end 164 approximates the tissue 160 to the cortical bone 176.

Figure 18D:
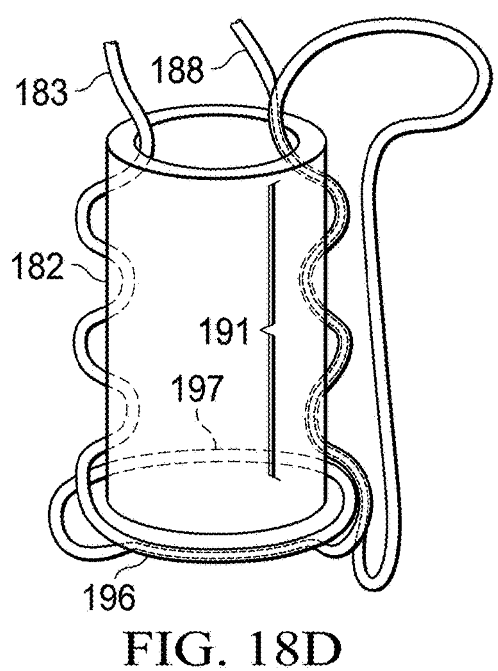
FIG. 18D is a perspective view of a soft anchoring implant comprising a distally disposed anchor alignment loop.

FIG. 18D shows another anchoring implant 182, first suture end 183 and second suture end 188 extending proximally from the anchoring implant. The suture is shown threaded or extending through the anchoring implant and through a portion of itself thereby forming a single suture locking region 191 along one lateral side of the anchoring implant. The anchoring implant additionally includes a centering or fixation zone 196 formed by the suture making a loop 197 about the distal end of the anchoring implant and being fed back through itself for a predetermined length 196. The zone 196 and loop 197 is interwoven at least in part with the soft anchoring implant which serves to maintain alignment of the locking cradle 191 during deployment and tissue approximation.

FIG. 18E shows an anchor assembly 180 including various instruments for inserting the anchoring implant 182 in a bone tunnel. The anchoring implant 182 is located within a distal section of an inserter tube 184. A die member 186 abuts the proximal end of the anchoring implant. The die member serves to prevent the anchor from backing out as it is deployed and the tissue is approximated.

A suture tail is shown commencing at 183, extending along a first lateral side of the anchoring implant 182, and forming a distal loop 197 and fixation zone 196. The suture further extends along a second lateral side, opposite to the first lateral side, and exits the anchoring implant at the proximal end to form a bend 199. From bend 199, a length 198 of suture continues in the distal direction along the exterior of soft anchoring implant.

The suture end 188 is shown extending distally from the soft anchor 182. In an application, and prior to positioning the inserter tube in a bone tunnel, the suture end 188 is passed through a tissue (not shown) and fed into snare loop 190. Snare tail 192 is then pulled proximally, drawing the suture end 188 through a hollow lumen portion of the suture to form the suture locking cradle region 191 as described in FIG. 18D.

The suture loop, and or suture ends may be pulled proximally from the anchoring implant to actuate the suture lock 191, binding the suture and prohibiting the suture loop from expanding.

A pin 194 (or another stabilizing feature) may be disposed at the distal tip of inserter tube to prevent distortion of the anchoring implant during snaring or other intermediate steps of the surgical procedure. In embodiments, the pin is an elongate rigid member removably located at distal end of the inserter tube, extending in a lateral direction through the distal end of the soft anchor, and perpendicular to the axis of the inserter tube.

Once the anchoring implant is connected to the tissue, and properly loaded with the suture, the pin 194 is removed. The distal end section of the inserter tube assembly 184 is advanced into a bone hole. The inserter tube is retracted, leaving the anchor in an undeployed configuration within the hole. The anchor bone lock is actuated to secure the anchoring implant 182 in the hole as described above. The suture ends may be further pulled to approximate the tissue to a final desired position and tension.

Although the suture paths shown in FIG. 18E extend along the sidewalls, in embodiments, the suture paths may extend from one sidewall to another in a zigzag pattern such as, for example, the suture pattern shown in FIG. 18B discussed herein.

In embodiments, the suture and anchor may be made of non-absorbable or absorbable materials. Example materials for the suture and implant include, without limitation, polyester and poliglecaprone respectively.

FIG. 19 shows another suture anchor assembly 200 including a first suture 202 and a separate independent suture 204. The first suture 202 is provided to deploy or lock the anchor in the bone and may be removed once the anchor implant has been deployed.

The second suture 204 is provided to lock the suture, and approximate the tissue to the anchor. The second suture 204 may be fed along the lateral and distal sides of the soft suture anchor, through the tissue, and back into a portion 206 of itself (outside of the anchor body) to achieve a suture lock/cradle. Except for the suture cradle portion 206 and tissue loop, the second length 204 of suture may follow the same path as the first length of the suture 202 through the anchoring implant. It is also noteworthy that in the embodiment shown in FIG. 19, the snaring step to form the suture-locking cradle is performed outside the anchor body. In contrast, various embodiments described herein require the snaring step to form the suture-locking cradle to be performed inside the anchor body.

FIGS. 20A and 20B show another anchoring implant 240 adapted to operate with two sutures: a first suture for locking the anchor in bone, and a second suture for binding the sutures. With reference to FIG. 20A, a first suture 242 extends in the proximal end of the anchor 240, down one lateral sidewall, across the distal end of the anchor, and up an opposing lateral sidewall. When the ends of the first suture are pulled, the anchor changes from an elongate cylindrical shape 240 as shown in FIG. 20A, to a short and more spherical shape 240' as shown in FIG. 20B. Consequently, the anchor may be selectively locked in the bone hole.

FIG. 20A also shows a plurality of wire snares 244, 246, 248, 250 extending through the suture 242. The various snares are for drawing a second suture through a plurality of tunnel regions of the first suture 242.

FIG. 20B shows the second suture (the first suture 242 not shown for ease of illustration) extending through the soft anchoring implant 240', to the tissue, back through the anchoring implant, and out the proximal end of the implant. The threading or snaring shown in FIGS. 20A and 20B, enables two lengths of sutures to be passed through each of the frictional suture locking passageways along the sidewalls. Indeed, second suture is drawn through each suture locking cradle for two passes. This is in contrast to some of the embodiments shown herein in which only one pass of the suture was made through a suture locking or frictional passageway.

Figure 20C:
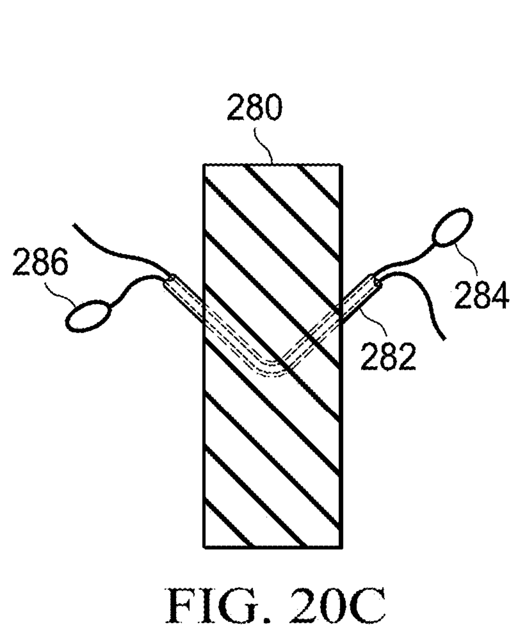
FIG. 20C is a side view of a soft anchoring implant comprising a first suture for creating an elongate suture binding region extending across the anchor body.
Figure 20D:
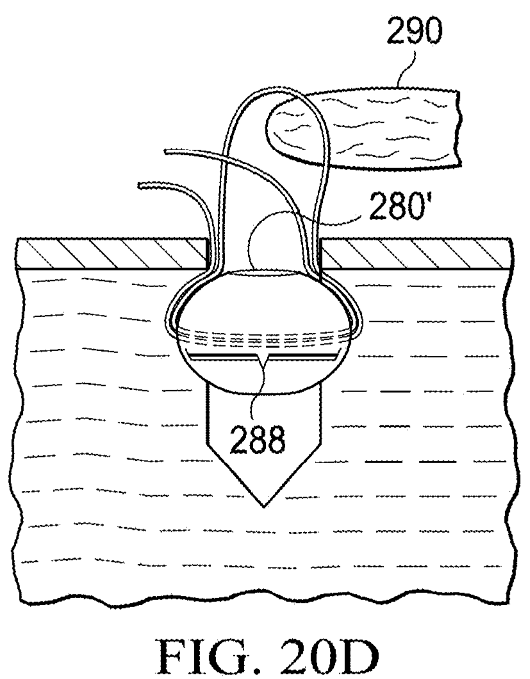
FIG. 20D is a side view of the soft anchoring implant shown in FIG. 20C, shown loaded with a second suture and deployed in a bone tunnel.

FIGS. 20C and 20D show an anchor assembly 280 having one long continuous friction lock instead of two or more short discrete regions. For example, the first suture 282 is shown extending from one side of the anchor, to the other side of the anchor. The snares 284 and 286 extend through the entire length of the first suture 282. Consequently, the frictional lock region shall include the entire length of the first suture through the anchor.

FIG. 20D shows a complete path of the second suture joining the tissue 290 to the anchor 280' (the first suture not shown for ease of illustration). The anchor 280' is also shown in its deployed bone-locked position. The frictional zone 288 shown in FIG. 20D is different than that shown in FIG. 20A in that the friction zone extends laterally through the anchor 280' in contrast to exiting at the anchor proximal/distal ends. The suture cradle 288 of FIG. 20D comprises one relatively long locking region rather than two or more distinct friction regions extending along the opposing sidewalls.

Figure 21:
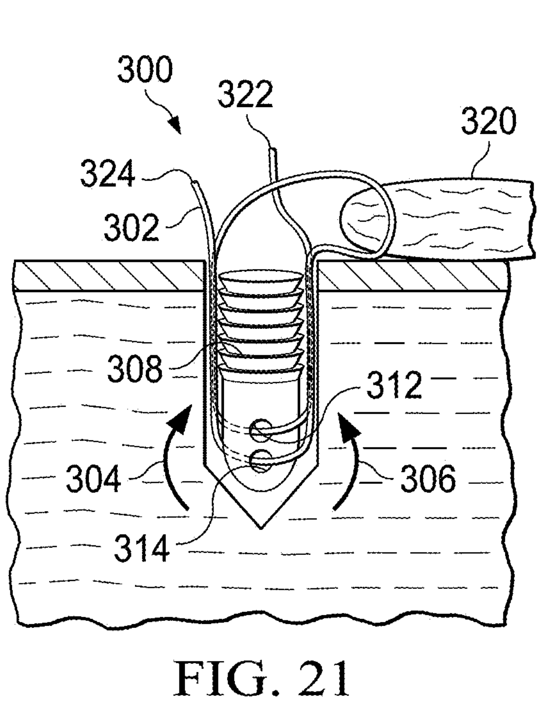
FIG. 21 is a side view of a hard anchoring implant, shown loaded with a suture and deployed in a bone tunnel.

As described herein it is to be understood that the anchoring assemblies may vary greatly and use alternate textiles and materials. FIG. 21, for example, shows a hard anchor assembly 300 in combination with suture lock mechanism(s) along at least one of the sidewalls of the anchor. One or more sutures 302 may be deployed about the anchor 300 in a path as shown in FIG. 21. Threading the suture along the path may be carried out with snares as described herein and as shown and described in FIGS. 1-6, for example. Consequently, two suture locking regions 304, 306 may be provided to lock the sutures in place prior to deploying the anchor 300. The anchor may then be deployed in the bone (not shown). An example of a hard anchor material is PGA or PLLA.

A wide variety of anchor shapes may be used in combination with the suture-locking mechanisms described herein. For example, as shown in FIG. 21, the anchor may include barbs or other bone locking features 308 to hold the anchor securely in the bone. Additionally, the suture may be looped around or threaded about protrusions, eyelets or other features 312, 314 present in the anchor to control the suture path, and bolster the desired tissue approximation. Suture ends 322, 324 may be pulled to approximate tissue 320 after the anchor is deployed in the bone tunnel.

Anchor with Simultaneous Bone and Suture Locking

Figure 22A:
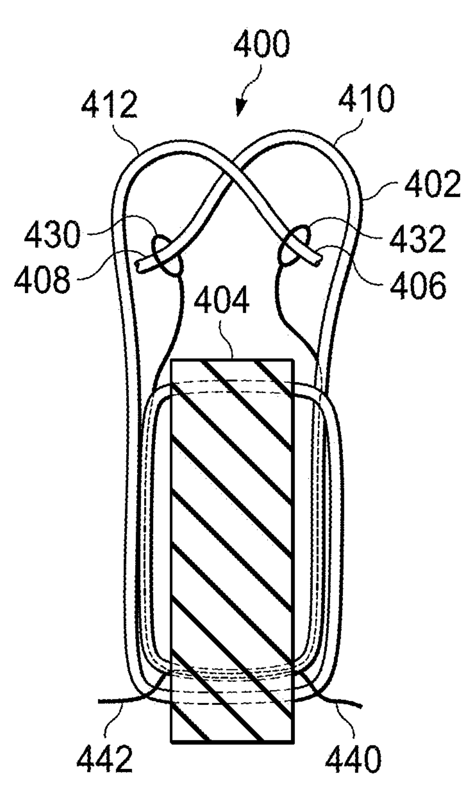
FIG. 22A is a side view of a soft anchoring implant comprising a suture path having a plurality of suture loops extending through a tissue.
Figure 22B:
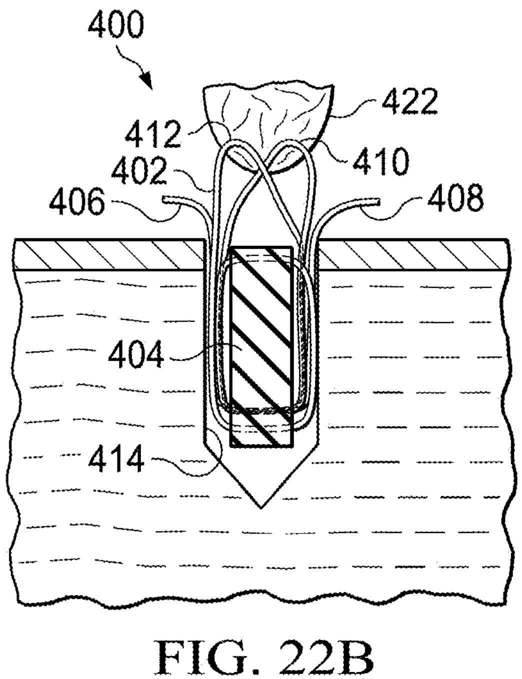
FIG. 22B is a side view of the soft anchoring implant shown in FIG. 20A, shown loaded with a suture and located in a bone tunnel.

FIGS. 22A and 22B show another suture locking anchor assembly 400. The embodiment shown in FIGS. 22A and 22B provides simultaneous a) locking of anchor implant 404 in a bone tunnel and b) securing the suture 402. With reference to FIG. 22A, a suture 402 is shown threaded around anchor body 404, terminating at tails 406, 408, and creating two precursor tissue loop lengths 410, 412.

Suture tails 406, 408 are passed through the tissue 422. Snares 430,432 capture the tails 406, 408 and draw the tails through the suture friction zones along the anchor sidewalls.

FIG. 22B shows anchor being inserted into the bone tunnel 414. Tails 406, 408 are shown pulled proximally which simultaneously locks the anchor in place and binds the sutures. Further tension applied to the suture tails approximates the tissue 422 to the bone.

Figure 23:
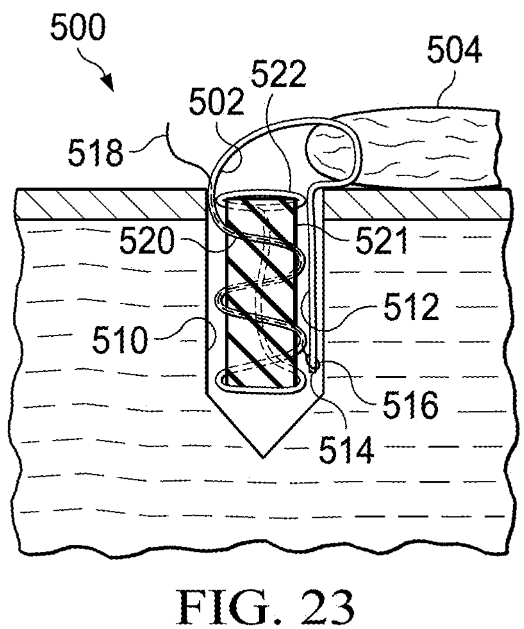
FIG. 23 is a side view of a soft anchoring implant comprising a proximally disposed anchor alignment loop.

FIG. 23 shows another anchor assembly 500 and suture 502 for approximating tissue 504 to bone. The anchor assembly 500 is shown positioned in a bone tunnel 510. Suture length 512 has been passed through tissue 504 and extends downward into the tunnel 510 along a sidewall.

In particular, suture 512 extends in a downward direction, between the anchor sidewall and a wall of the bone tunnel. Suture 512 terminates at suture tail or end 514. A snare 516 extends through a suture capture zone 520 in the suture. The suture capture zone is wound about and interwoven with the anchor body 521. By pulling on snare proximal end 518, a suture length may be drawn through the suture friction zone or locking cradle 520. The suture tail is then pulled proximally as desired to lock the suture, deploy the anchor in the bone, and to further approximate the tissue.

Fixation loop 522 is provided to maintain alignment of the anchor and cradle inside the bone tunnel. Consequently, as the anchor is deployed and suture locked, the anchor body is urged into the tunnel instead of being pulled out of the tunnel.

While preferred embodiments of this disclosure have been shown and described, modifications thereof can be made by one skilled in the art without departing from the scope or teaching herein. The embodiments described herein are exemplary only and are not intended to be limiting. Because many varying and different embodiments may be made within the scope of the present inventive concept, including equivalent structures, materials, or methods hereafter thought of, and because many modifications may be made in the embodiments herein detailed in accordance with the descriptive requirements of the law, it is to be understood that the details herein are to be interpreted as illustrative and not in a limiting sense.

We claim:

1. A method of securing a bone to a repair tissue with an anchor assembly, without the need to tie a knot, the method comprising:

placing the anchor assembly into the bone, the anchor assembly including an all-suture anchor body and a suture threaded along the all-suture anchor body, the all-suture anchor body being tubular and including a proximal and distal region and wherein placing locates the distal region distally in the bone, and wherein the suture includes a lumen and has a suture end extending proximally from the all-suture anchor body, the suture also including a suture repair loop, the suture repair loop including;

a knotless locking region that includes a length of the suture extending through the suture lumen, the knotless locking region extending along and within the all-suture anchor body, the suture fixedly coupled to the all-suture anchor body to limit movement of the knotless locking region location relative to the all-suture anchor body; and a tissue loop portion extending proximally from the all-suture anchor body proximal region; and expanding the all-suture anchor body to secure the anchor assembly with the bone.

2. The method of claim 1 further comprising applying tension to the suture end to expand the all-suture anchor body.

3. The method of claim 1 further comprising looping the tissue loop portion around the repair tissue to couple the anchor assembly to the repair tissue.

4. The method of claim 3 further comprising applying tension to the suture end to reduce the tissue loop portion and draw the repair tissue towards the bone.

5. The method of claim 4 further comprising applying tension to the suture end after the tissue loop portion is reduced to radially decrease the knotless locking region and knotlessly lock the suture repair loop.

6. The method of claim 1 wherein the knotless locking region extends along a lumen of the all-suture anchor body.

7. The method of claim 1 wherein suture repair loop is repeatedly woven along and through a first side of the all-suture anchor body and also repeatedly woven along and through an opposite side of the all-suture anchor body.

8. The method of claim 7 wherein the knotless locking region extends along and is repeatedly interwoven along only the first side of the all-suture anchor body.

9. The method of claim 1 wherein the suture is fixedly coupled to a distal most end of the all-suture anchor body, distal to the knotless locking region.

10. A method of securing a bone to a repair tissue with an anchor assembly, without the need to tie a knot, the method comprising:

placing the anchor assembly into the bone, the anchor assembly including an all-suture anchor body and a suture interwoven repeated along and through the all-suture anchor body, the all-suture anchor body being tubular and including a proximal and distal region and wherein placing locates the distal region distally in the bone, and wherein the suture includes a lumen and has a suture end extending proximally from the all-suture anchor body and a suture repair loop, the suture repair loop including;

a knotless locking region wherein the suture is passed through the suture lumen, the knotless locking region interwoven repeatedly along and through the all-suture anchor body, the suture fixedly coupled to the all-suture anchor body to maintain the knotless locking region location relative to the all-suture anchor body; and a tissue loop portion extending proximally from the all-suture anchor body proximal region;

expanding the all-suture anchor body after placing the anchor assembly to secure the anchor assembly with the bone; and applying tension to the suture end to reduce the suture repair loop.

11. The method of claim 10 further comprising applying tension to the suture end to expand the all-suture anchor body.

12. The method of claim 10 further comprising looping the tissue loop portion around the repair tissue.

13. The method of claim 12 further comprising applying tension to the suture end to reduce the tissue loop portion and draw the repair tissue towards the bone.

14. The method of claim 10 further comprising applying tension to the suture end to radially decrease the knotless locking region and knotlessly lock the suture repair loop.

15. The method of claim 10 wherein the knotless locking region extends along only a first side of the all-suture anchor body.

16. A method of securing a bone to a repair tissue with an anchor assembly, without the need to tie a knot, the method comprising:

placing the anchor assembly into the bone, the anchor assembly including an all-suture anchor body and a suture interwoven repeatedly along and through the all-suture anchor body, the all-suture anchor body being tubular and including a proximal and distal region and wherein placing locates the distal region distally in the bone, and wherein the suture includes a lumen and has a suture end extending proximally from the all-suture anchor body, the suture formed in a suture repair loop, the suture repair loop including;

a knotless locking region wherein the suture is passed through the suture lumen, the knotless locking region interwoven repeatedly along and through a first side of the all-suture anchor body, the suture also fixedly coupled to the distal region of the all-suture anchor body and distal to the knotless locking region to maintain the knotless locking region location relative to the all-suture anchor body; and a tissue loop portion extending proximally from the all-suture anchor body proximal region;

expanding the all-suture anchor body after placing the anchor assembly to secure the anchor assembly with the bone;

applying tension to the suture end to reduce the suture repair loop and then applying tension to the suture end to radially decrease the knotless locking region and knotlessly lock the suture repair loop.

17. The method of claim 16 further comprising looping the tissue loop portion around the repair tissue.

* * * * *